United States Patent [19]

Auerbach et al.

[11] Patent Number: 5,649,947

[45] Date of Patent: *Jul. 22, 1997

[54] SURGICAL INSTRUMENT

[75] Inventors: Burt J. Auerbach, Pasadena; George V. Shutt, Glendora, both of Calif.

[73] Assignee: Arthrotek, Inc., Warsaw, Ind.

[ * ] Notice: The term of this patent shall not extend beyond the expiration date of Pat. No. 5,443,475.

[21] Appl. No.: 517,501

[22] Filed: Aug. 21, 1995

Related U.S. Application Data

[63] Continuation of Ser. No. 925,225, Aug. 3, 1992, Pat. No. 5,443,475, which is a continuation of Ser. No. 612,106, Nov. 9, 1990, abandoned.

[51] Int. Cl.$^6$ ..................................................... A61B 17/32
[52] U.S. Cl. .......................... 606/170; 606/83; 606/174; 128/751
[58] Field of Search ...................... 604/22; 606/205–208, 606/170, 167, 174, 83, 79, 184; 128/751

[56] References Cited

U.S. PATENT DOCUMENTS

| | | |
|---|---|---|
| 327,204 | 9/1885 | Somers . |
| 495,668 | 4/1893 | Fete . |
| 2,547,707 | 4/1951 | Karle . |
| 2,568,234 | 9/1951 | Haufrect . |
| 2,668,537 | 2/1954 | Kapp . |
| 2,698,621 | 1/1955 | Fernandez . |
| 2,702,550 | 2/1955 | Rowe . |

(List continued on next page.)

FOREIGN PATENT DOCUMENTS

| | | |
|---|---|---|
| 0313820 | 5/1989 | European Pat. Off. . |
| 0401728 | 12/1990 | European Pat. Off. . |
| 1037403 | 9/1953 | France . |
| 230503 | 1/1911 | Germany . |
| 3303349 | 8/1984 | Germany . |
| 8712271 | 1/1988 | Germany . |
| 6729 | 11/1895 | Sweden . |
| 649420 | 3/1979 | U.S.S.R. . |
| 812270 | 3/1981 | U.S.S.R. . |
| 2161707 | 1/1986 | United Kingdom . |
| 2198950 | 6/1988 | United Kingdom . |

OTHER PUBLICATIONS

Zimmer Brochure, "The Master Series" 1990.
Zimmer News Release, No. 606–83, Oct. 11, 1966.
Karl Storz, Catalog Pages, Endoscopic Diagnosis, Surgery and Treatment of Paranasal Sinus Mycoses, Endoscopes and Instruments as used by Professor W. Messerklinger and H. Stammberger, Mar. 1985.

*Primary Examiner*—Michael H. Thaler
*Attorney, Agent, or Firm*—Barnes & Thornburg

[57] ABSTRACT

A surgical instrument has an elongate support shaft, a tip assembly permanently attached to the shaft, a cutting jaw which opens in a backward facing direction and which is laterally offset from the longitudinal axis of the support shaft, and a rod extending coaxially with the elongate support shaft for applying closing and opening forces to the cutting jaw. The tip assembly comprises a stationary portion and a movable portion having respective tissue cutting edges which define the cutting jaw. The stationary portion of the tip assembly is permanently attached to the distal end of the support shaft, and the movable portion of the tip assembly is pivotally attached to a distal end of the stationary portion. The stationary portion of the tip assembly has a plurality of cutting edges which define an opening which extends axially adjacent the longitudinal axis of the support shaft. The movable portion has corresponding cutting edges which cooperate with the cutting edges of the stationary portion to define the cutting jaw. The cutting jaw has a fully open position in which the movable element extends outwardly from the longitudinal axis and toward a proximal end of the elongate shaft at an angle of approximately 60°. The cutting jaw has a fully closed position in which the cutting element is disposed within the opening in the stationary portion of the tip assembly. The tip assembly has an overall height dimension, when the cutting element is in the fully closed position, which is substantially equal to a corresponding cross-sectional dimension of the elongate support shaft.

18 Claims, 5 Drawing Sheets

U.S. PATENT DOCUMENTS

| | | |
|---|---|---|
| 3,308,828 | 3/1967 | Pippin . |
| 3,721,245 | 3/1973 | Campbell . |
| 3,752,161 | 8/1973 | Bent . |
| 4,122,856 | 10/1978 | Mosior et al. . |
| 4,243,047 | 1/1981 | Olsen . |
| 4,499,899 | 2/1985 | Lyons, III . |
| 4,590,936 | 5/1986 | Straub et al. . |
| 4,644,951 | 2/1987 | Bays . |
| 4,662,371 | 5/1987 | Whipple et al. . |
| 4,733,663 | 3/1988 | Farley . |
| 4,763,669 | 8/1988 | Jaeger . |
| 4,777,948 | 10/1988 | Wright . |
| 4,944,093 | 7/1990 | Falk . |
| 5,112,346 | 5/1992 | Hiltebrandt et al. . |
| 5,152,780 | 10/1992 | Honkanen et al. . |
| 5,443,475 | 8/1995 | Auerbach et al. . |

SURGICAL INSTRUMENT

This is a continuation of application Ser. No. 07/925,225, filed Aug. 3, 1992 (now U.S. Pat. No. 5,443,475), which was a continuation of application Ser. No. 07/612,106 filed Nov. 9, 1990 (now abandoned).

BACKGROUND AND SUMMARY OF THE INVENTION

This invention relates generally a surgical instrument and, more particularly, to a forceps instrument which may be used in arthroscopic surgical procedures involving the knee, the shoulder, and other joints.

Arthroscopic surgery of the knee, the shoulder, and other joints is a commonly accepted surgical procedure. A number of instruments have been developed for such surgeries, including those shown in U.S. Pat. Nos. 4,662,371 and 4,944,093. Instruments such as those shown in these patents are typically used with an arthroscope which allows the surgeon to view the interior of the joint through an eye piece or, alternatively, on a video display screen.

Efficient arthroscopic triangulation generally requires wide separation of the viewing instrument and the operating instrument. Normally, this is not a problem and has been made easier by the use of optical devices having angled fields of view, as well as by the use of curved operating instruments. However, on frequent occasions involving certain joint locations, such as the anterior horn of the lateral meniscus in the knee and the inner edge of the anterior glenoid labrum in the shoulder, effective triangulation is difficult. In these locations, the optimum viewing portal is often the best portal for the operating instrument.

A basket forceps is often used to remove tissue associated with tears of the lateral meniscus in the knee and the anterior glenoid labrum in the shoulder. The conventional design is a forward cutting instrument which may slice through or nibble off a portion of the torn tissue. A basket forceps cuts most efficiently when the tissue to be cut is approached directly with an open instrument jaw. For tears in the posterior portion of the lateral meniscus, for instance, conventional instruments work well when entering the knee joint from an anterior medial or anterior lateral portal. However, torn tissue in the anterior horn of the lateral meniscus cannot be easily approached with a forward cutting device. The surgeon must either work awkwardly with a forward cutting basket forceps or create an instrument portal close to the viewing portal, which makes triangulation awkward and difficult. These difficulties increase operating time and surgeon frustration.

An object of the present invention is to provide a surgical instrument which has an instrument jaw which opens in a generally backward-facing direction (i.e., in a direction which faces the instrument shaft and handle) to facilitate the cutting of body tissue in certain joint locations.

Another object of the present invention is to provide a surgical instrument in which the cutting plane of the instrument is laterally adjacent (or offset from) the longitudinal axis of the instrument support shaft to maintain a narrow instrument profile and to facilitate passage of the instrument through the operating portal.

Yet another object of the present invention is to provide a surgical instrument which is especially well-suited for surgical procedures involving the anterior horn of the lateral meniscus of the knee, the inner edge of the anterior glenoid labrum in the shoulder, and other particular joint locations.

These and other objects of the invention are achieved in a surgical instrument for cutting body tissue which comprises an axially elongate support shaft, a tip assembly permanently attached to the distal end of the shaft, and means extending coaxially with the elongate support shaft for actuating the instrument. The tip assembly comprises a stationary portion and a movable portion having respective tissue cutting edges which define a cutting jaw which opens toward the elongate support shaft. The cutting jaw is laterally offset from the longitudinal axis of the shaft. The means for actuating the instrument comprises means for applying a closing force and an opening force to the movable portion of the cutting jaw.

In a preferred embodiment of the invention, the stationary portion of the tip assembly is permanently attached to the distal end of the support shaft, and the movable portion of the tip assembly is pivotally attached to a distal end of the stationary portion. The stationary portion of the tip assembly comprises a plurality of cutting edges which define an opening in the stationary portion which extends axially adjacent a longitudinal axis of the support shaft. The movable portion of the tip assembly comprises a cutting element having a plurality of cutting edges which cooperate with the cutting edges of the stationary portion to define the cutting jaw.

The cutting jaw has a fully open position in which the cutting element extends outwardly from the longitudinal axis and toward a proximal end of the elongate shaft at an angle of approximately 60°. The cutting jaw has a fully closed position in which the cutting element is disposed within the opening in the stationary portion of the tip assembly. The tip assembly has an overall height dimension, when the cutting element is in the fully closed position, which is substantially equal to a corresponding cross-sectional dimension of the elongate support shaft.

In the preferred embodiment of the invention disclosed, the means extending coaxially with the elongate support shaft for applying a closing force and an opening force to the movable portion of the cutting jaw comprises a wire rod. A distal end of the wire rod is flattened and pivotally attached to the moving portion of the tip assembly.

Other objects, advantages and novel features of the present invention will become apparent from the following detailed description of the invention when considered in conjunction with the accompanying drawings.

DETAILED DESCRIPTION OF THE DRAWINGS

Figures 1A, 1B:
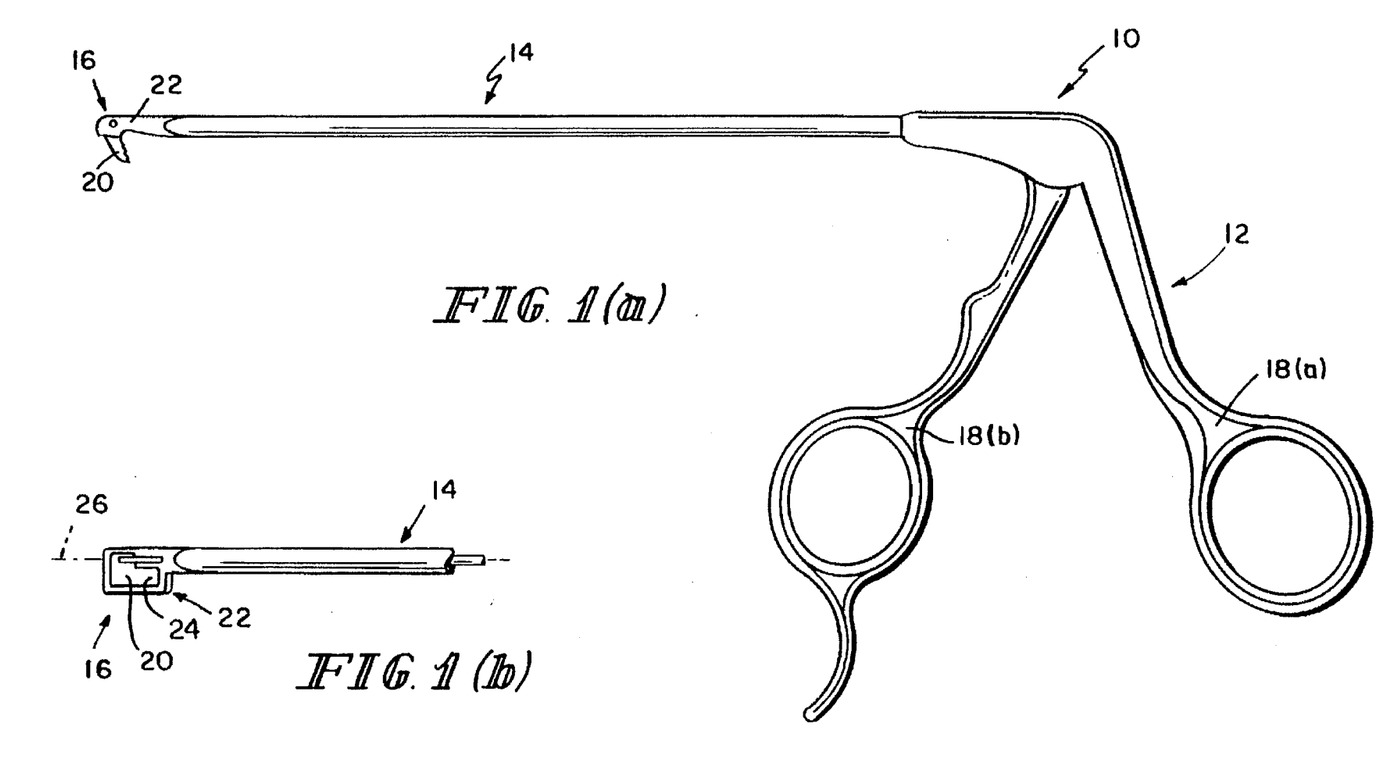
FIG. 1(a) shows a side view of a surgical instrument constructed in accordance with the principles of the present invention.
FIG. 1(b) shows a bottom view of a portion of the instrument of FIG. 1(a).

FIG. 1(a) shows a surgical instrument 10 which comprises a handle portion 12, an axially elongate support shaft 14 and a tip assembly 16. Handle portion 12 includes a stationary half 18(a) and a movable half 18(b) which may be closed in well-known scissor-like fashion to actuate the instrument, as will be described in additional detail below.

FIG. 1(b) shows a bottom view of shaft 14 and tip assembly 16 of instrument 10. Tip assembly 16 includes a movable cutter element 20 which is pivotally attached to a distal end of a stationary portion 22 of assembly 16. As will be described more fully in connection with FIGS. 3(a) and 3(b), stationary portion 22 includes a plurality of cutting edges which define an opening 24 which is positioned laterally adjacent longitudinal axis 26 of support shaft 14. When a closing force is applied to handle portion 12 to actuate the instrument, cutter element 20 rotates upwardly and in the counterclockwise direction, as viewed in FIG. 1(a), toward the longitudinal axis and the proximal end of support shaft 14. The cutting edges of element 20 and stationary portion 22 sever tissue which is then confined in opening 24.

Figure 2A:
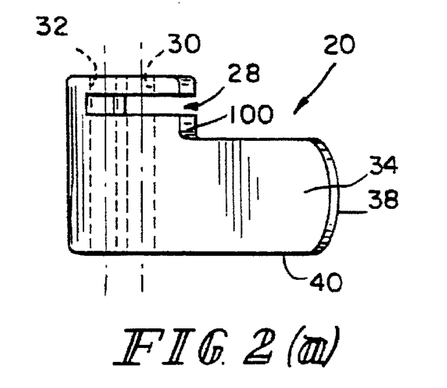
FIG. 2(a) shows a plan view of a cutting element used in an instrument constructed in accordance with the principles of the present invention.
Figure 2B:
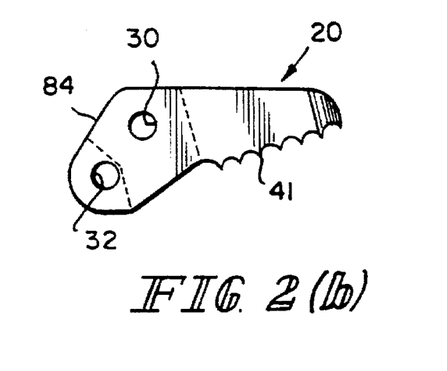
FIG. 2(b) shows a side view of the cutting element of FIG. 2(a).

FIGS. 2(a) and 2(b) show plan and side views, respectively, of a preferred embodiment of cutting element 20. Cutting element 20 includes a slot 28 which, in the preferred embodiment illustrated, receives the flattened end 76 of a wire rod 74 used to actuate the cutter mechanism (see FIGS. 4(a)–(c)). A pair of through holes 30 and 32 are provided to receive pins which pivotally connected cutter element 20 to wire rod 74 and stationary portion 22 of tip assembly 16, respectively. A cutter portion 34 of cutting element 20 is defined on three sides by cutting edges 36, 38 and 40. Edges 36 and 40, and the connecting surface 41 of cutter portion 34, are "scalloped," as illustrated in FIG. 2(b), to define a gripping surface for contacting the portion of body tissue to be severed.

Figure 3A:
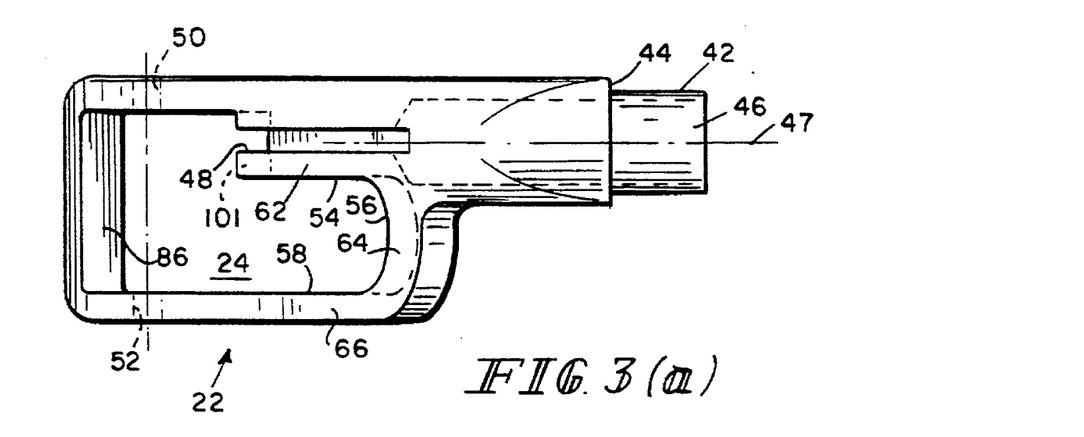
FIG. 3(a) shows a plan view of a stationary portion of a tip assembly used in an instrument constructed in accordance with the principles of the present invention.
Figure 3B:
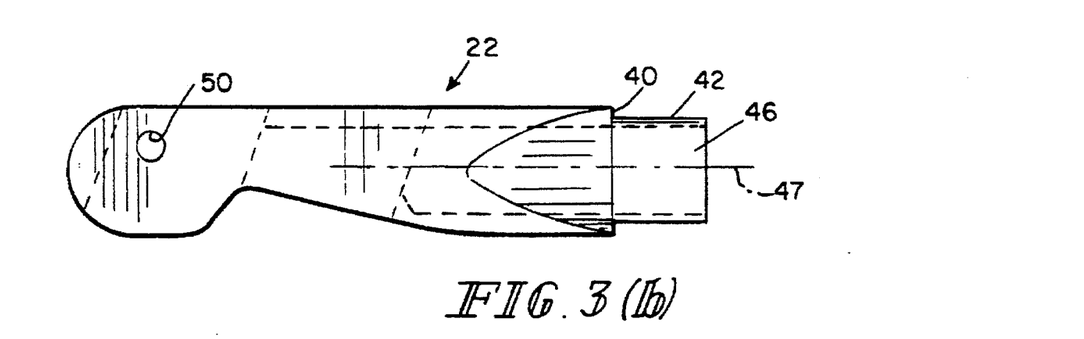
FIG. 3(b) shows a side view of the stationary portion of the tip assembly shown in FIG. 3(a).
Figure 4A:
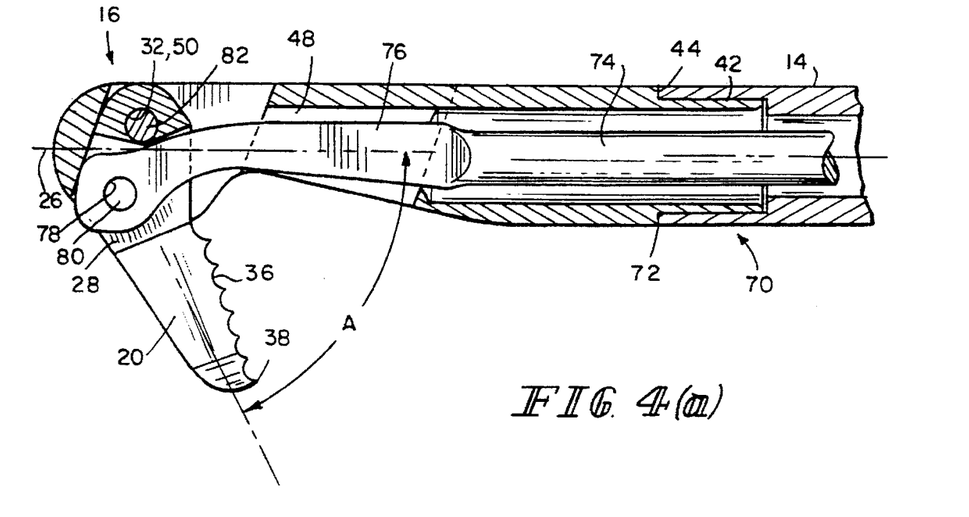
FIG. 4(a) shows, in partial cross-section, the tip assembly of a surgical instrument constructed in accordance with the principles of the present invention with the cutting jaw positioned in the fully opened position.
Figure 4B:
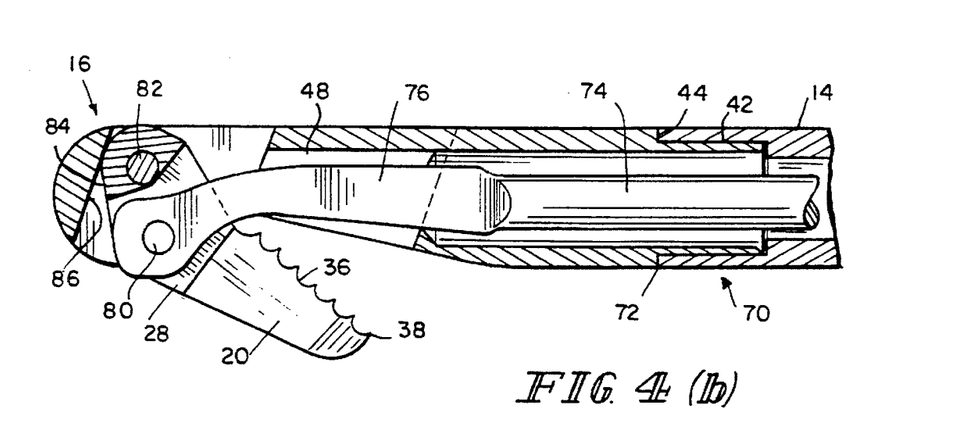
FIG. 4(b) shows the tip assembly of FIG. 4(a) with the cutting jaw positioned in the half open position.
Figure 4C:
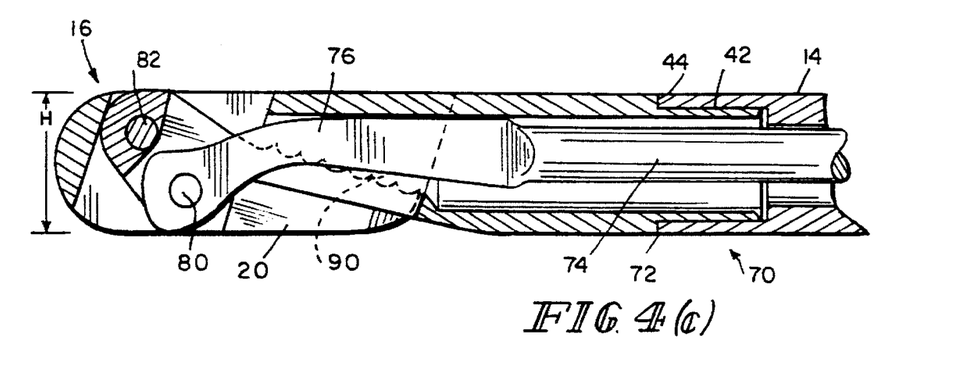
FIG. 4(c) shows the cutting tip assembly of FIG. 4(a) with the cutting jaw positioned in the fully closed position.

FIGS. 3(a) and 3(b) show plan and side views, respectively, of stationary portion 22 of tip assembly 16. Portion 22 includes a circumferentially reduced portion 42 and an annular shoulder 44 which are ultimately positioned adjacent to, and are permanently attached to, a distal end 70 of elongate shaft 14 (see FIGS. 4(a)–(c)). Stationary portion 22 further includes an internal bore 46 which extends along a centerline 47 which is coaxially aligned with centerline 26 of shaft 14 when top assembly 16 is attached to shaft 14. Bore 46 terminates in a slot 48 which receives flattened end 76 of wire rod 74, as illustrated in FIGS. 4(a)–(c). A pair of coaxially aligned holes 50 and 52 are provided, and are aligned with hole 32 in element 20 when the assembly 16 is assembled.

Stationary portion 22 includes cutting edges 54, 56 and 58 which define three sides of opening 24. Opening 24 extends laterally adjacent centerline 47 (and thus longitudinal axis 26) and is offset from centerline 47, as shown in FIG. 3(a). As illustrated in FIGS. 3(b) and 4(c), this arrangement provides for maintaining a low overall height profile when cutter element 20 is in the fully closed position within opening 24. Cutting edges 54, 56 and 58 cooperate with edges 36, 38 and 40, respectively, to exert a cutting action on the tissue to be severed. Sidewalls, 62, 64 and 66 immediately adjacent edges 54, 56 and 58, respectively, and cutting portion 34, when cutter element 20 is in the fully closed position, form a "basket" which confines and holds the body tissue severed by the cutting action of the instrument.

FIG. 4(a) shows an enlarged partial cross-sectional view of tip assembly 16 with cutter element 20 positioned in the fully open position. Tip assembly 16 is permanently mounted, such as by welding, to the distal end 70 of elongate shaft 14. In the particular embodiment illustrated, distal end 70 of shaft 14 receives portion 42 within its hollow inner bore, and abuts annular shoulder 44 so as to produce a smooth, continuous profile in the area of joint 72. Extending coaxially with elongate shaft 14 is wire rod 74 which is connected on its proximal end to handle portion 12 (not shown). Wire rod 74 has a flattened distal end 76 which extends through slot 48 in stationary portion 22 and into slot 28 in cutter element 20. A transverse hole 78 is provided near the distal end of flattened end 76. Hole 78 is aligned with hole 30 in cutter element 20. Holes 30 and 78 receive pin 80 which pivotally connects flattened end 76 and cutter element 20. Pin 82 is also provided through hole 32 of cutter element 20 and holes 50 and 52 of stationary portion 22 to pivotally connect element 20 to stationary portion 22.

Cutter element 20 is shown in FIG. 4(a) in the fully open position. The angle A which cutter element 20 defines relative to longitudinal axis 26 is controlled by the interaction of surfaces 84 and 86 on cutter element 20 and stationary portion 22, respectively (see FIGS. 2(b) and 3(a)). In the preferred embodiment illustrated, angle A is approximately 60°.

FIG. 4(b) shows cutter element 20 in the partially closed position. As cutter element 20 moves toward stationary portion 22 (i.e., as angle A decreases), the "scalloped" surface 41 of element 20 lifts and positions the tissue to be severed. The angle A at which element 20 begins its movement may be important to assure proper lifting and positioning of the tissue in particular situations.

FIG. 4(c) shows tip assembly 16 with cutter element 20 in the fully closed position. The final positioning of cutter element 20 when fully closed is controlled by the interaction of surface 100 on cutter element 20 and surface 101 on stationary portion 22 (i.e., these surfaces abut in the fully closed position). The overall profile, as viewed from the side, of tip assembly 16 with cutter element 20 in the fully closed position is substantially uniform and continuous, and approximately equal to the cross-sectional profile of shaft 14, as is apparent in FIG. 4(c). This overall profile is represented in FIG. 4(c) by dimension H. Top surface 41 of cutter element 20 and sidewalls 62, 64 and 66 of stationary portion 22 form a "basket" 90 which receives the tissue severed by the respective cutting edges of element 20 and stationary portion 22. The positioning of "basket" 90 laterally adjacent (i.e. offset from ) axis 26 of shaft 14 allows for maintaining the compact profile illustrated by dimension H.

Figure 5A:
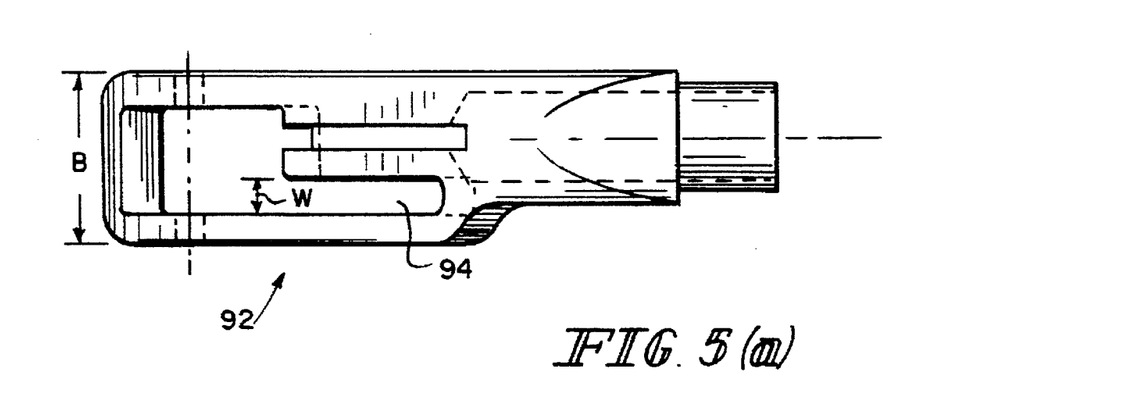
FIG. 5(a) shows a plan view of an alternative embodiment of a stationary portion of a tip assembly for use with a surgical instrument constructed in accordance with the principles of the present invention.
Figure 5B:
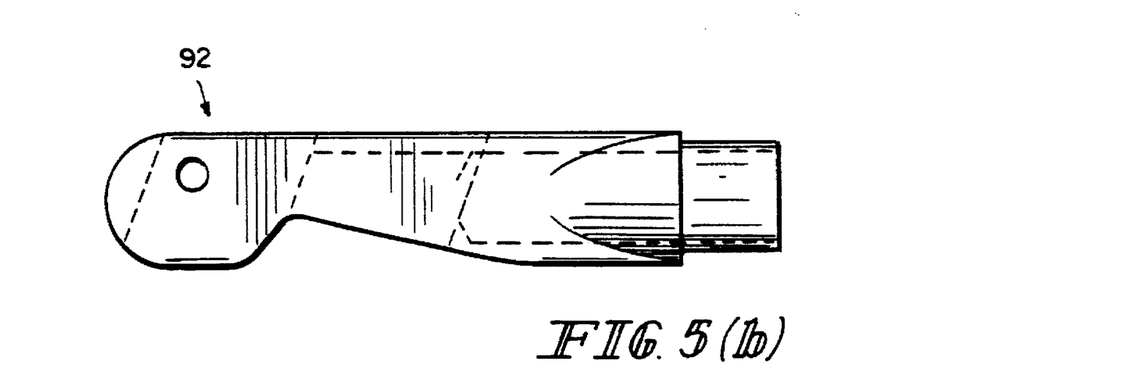
FIG. 5(b) shows a side view of the stationary portion of the tip assembly of FIG. 5(a).
Figure 6A:
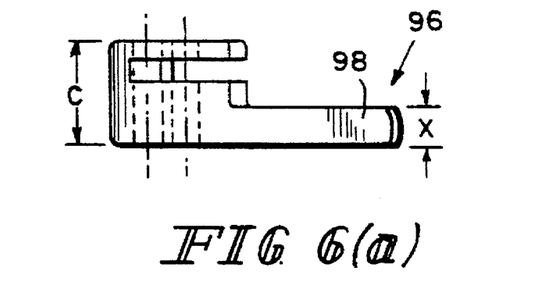
FIG. 6(a) shows a plan view of a cutter element used with the stationary portion of the tip assembly shown in FIGS. 5(a) and 5(b).
Figure 6B:
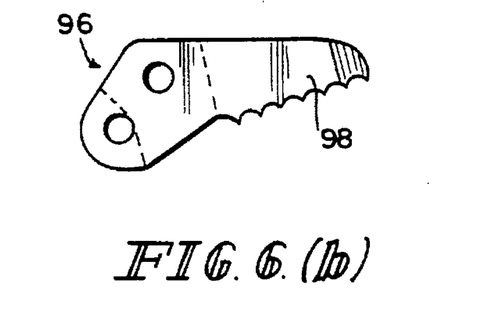
FIG. 6(b) shows a side view of the cutter element of FIG. 6(a).

FIGS. 5(a) and 5(b) show plan and side views, respectively, of a modified embodiment of the stationary portion of tip assembly 16. Stationary portion 92 of FIGS. 5(a) and 5(b) is similar in all respects to stationary portion 22 of FIGS. 3(a) and 3(b) except for the width of the area 94, represented by dimension W, which defines the width of body tissue severed in the cutting procedure, and the overall width represented by dimension B. FIGS. 6(a) and 6(b) show plan and side views, respectively, of a cutter element 96 which is similar in all respects to cutter element 20 shown in FIGS. 2(a) and 2(b) except for the overall width C and the width X of cutting portion 98. These dimensions are chosen to allow element 96 to be assembled with stationary portion 92 such that the overall width of the tip assembly, as represented by dimension B, is close to the overall cross-sectional width of shaft 14. This arrangement provides a very compact configuration when cutter element 96 is in the fully closed position. This facilitates insertion and withdrawal of the instrument into and from the affected joint or body region.

Figure 7:
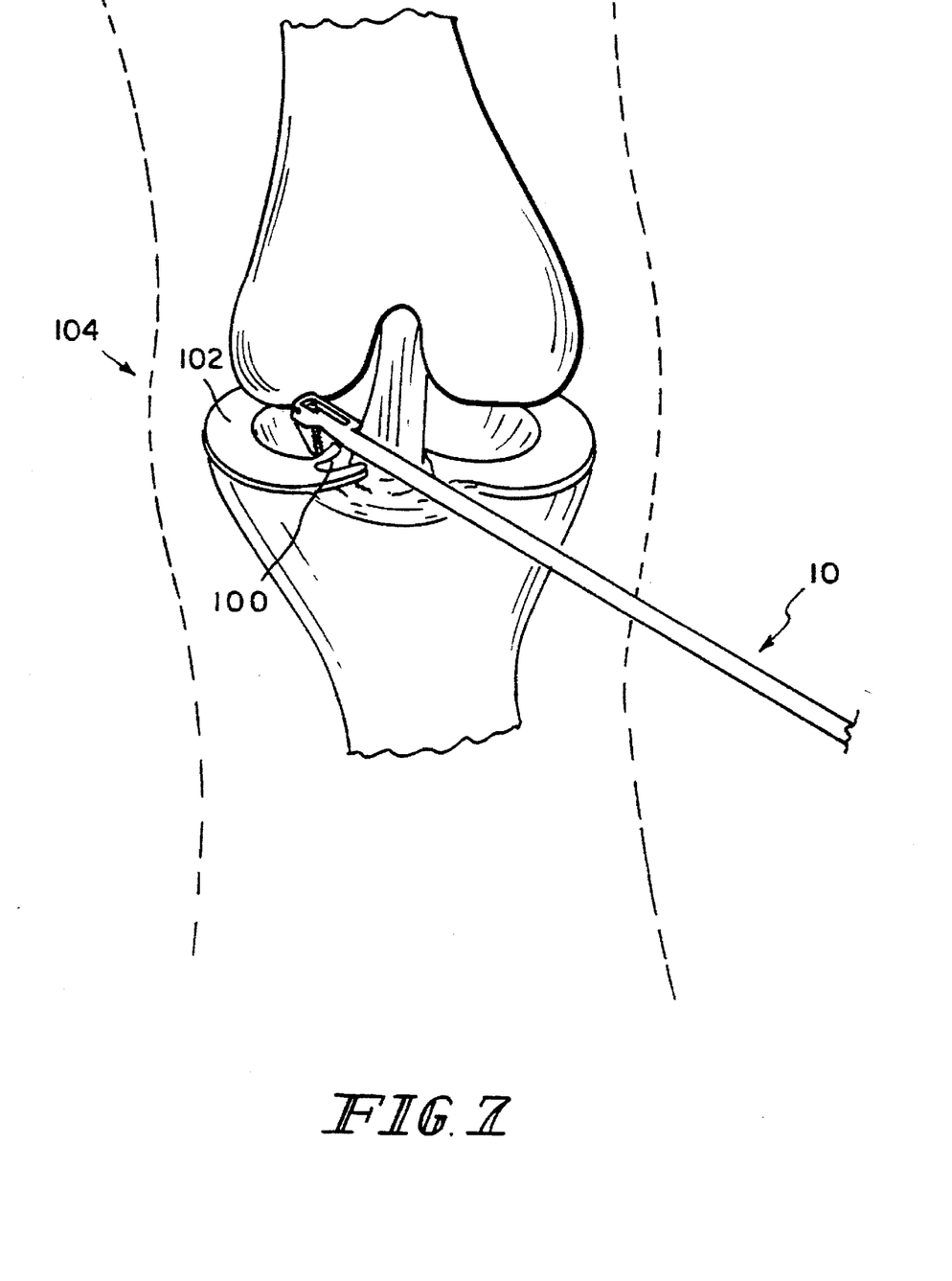
FIG. 7 shows a representation of a knee joint with the instrument of FIG. 1(a) inserted into the joint.

FIG. 7 shows a portion of instrument 10 in position for surgical removal of a torn portion 100 of the anterior horn of the lateral meniscus 102 in a knee joint 104. A basket forceps cuts most efficiently when the tissue to be cut is approached directly with an open instrument jaw. The "backbiting" configuration of instrument 10 allows such an approach to torn portion 100. Such an approach from an anterior portal would not be practical using conventional forward cutting instruments, even using instruments having curved shafts or angled tips.

Efficient arthroscopic triangulation requires wide separation of the viewing instrument and the operating instrument. In the arrangement of FIG. 7, a suggested configuration for removing torn portion 100 of the lateral meniscus of joint 104 would be to place a 30° arthroscope in the anterior inferio-medial portal directed anteriorly, while placing instrument 10 in the anterior inferio-lateral portal passing directly over torn portion 100. This configuration improves both the viewing and cutting angles relative to those available using conventional instrumentation.

From the preceding description of the preferred embodiments of the invention, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. A surgical instrument for cutting body tissue, comprising:
   an elongate support shaft;
   a tip assembly attached to a distal end of the support shaft, said tip assembly comprising a stationary portion and a movable portion, a distal end of said movable portion being pivotally connected to a distal end of the stationary portion so as to form a cutting jaw; and
   means extending coaxially with the support shaft for applying closing and opening forces to the movable portion of the cutting jaw;
   wherein said stationary portion comprises a first cutting edge extending substantially parallel to and laterally adjacent a central longitudinal axis of the support shaft, and a second cutting edge extending substantially parallel to the first cutting edge, and a third cutting edge extending from a proximal end of said first cutting edge to a proximal end of said second cutting edge; and
   wherein said movable portion comprises first, second and third cutting edges which cooperate, respectively, with the first, second and third cutting edges of the stationary portion.

2. A surgical instrument according to claim 1, wherein said stationary portion further comprises first and second sidewalls, extending laterally adjacent and substantially parallel to the longitudinal axis of the support shaft, and wherein said sidewalls have openings formed therein for receiving respective ends of a pivot pin which extends through, and forms a pivot axis of, said movable portion of the tip assembly.

3. A surgical instrument according to claim 2, wherein said first, second and third cutting edges lie between substantially parallel planes extending, respectively, substantially transversely through the respective ends of the pivot pin.

4. A surgical instrument according to claim 2, wherein said stationary portion further comprises a third sidewall extending substantially orthogonally from a distal end of the first sidewall to a distal end of the second sidewall.

5. A surgical instrument according to claim 2, wherein said means extending coaxially with the support shaft comprises a wire rod having a flattened distal end which is pivotally connected to the movable portion of the tip assembly.

6. A surgical instrument according to claim 5, wherein said movable portion of the tip assembly is provided with a slot which receives the distal end of the wire rod, and wherein the distal end of the wire rod is pivotally attached to opposing sidewalls of the slot.

7. A surgical instrument according to claim 6, wherein the pivotable connection between the wire rod and the movable portion of the tip assembly, and the first, second and third cutting edges, lie between substantially parallel planes extending, respectively, substantially transversely through the respective ends of the pivot pin.

8. A surgical instrument according to claim 1, wherein a surface of said movable portion partially defined by said first, second and third cutting edges is scalloped to facilitate the positioning of tissue to be cut by the instrument.

9. A surgical instrument according to claim 1, wherein the cutting jaw has a fully open position in which the movable portion extends outwardly from the longitudinal axis and toward a proximal end of the elongate shaft at an angle of approximately 60°.

10. A surgical instrument according to claim 1, wherein the cutting jaw has a fully open position in which the movable portion extends outwardly from the longitudinal axis and toward a proximal end of the elongate shaft at an angle which is controlled by interaction of a surface on said movable portion and a surface of the stationary portion.

11. A surgical instrument for cutting body tissue, comprising:
   a support shaft having a longitudinal axis;
   a tip assembly attached to a distal end of the support shaft, said tip assembly comprising a stationary portion and a movable portion, said stationary portion having a pair of opposing sidewalls;
   a pivot pin connecting a distal end of the movable portion between distal ends of the opposing sidewalls of the stationary portion so as to form a cutting jaw; and
   an elongate member extending coaxially with the support shaft and pivotally connected to the movable portion of the tip assembly for applying closing and opening forces to the movable portion of the cutting jaw;
   wherein said stationary and movable portions comprise a plurality of cooperating cutting edges disposed between substantially parallel planes which extend substantially transversely through the pivot pin at the distal ends of the opposing sidewalls.

12. A surgical instrument according to claim 11, wherein said elongate member comprises a wire rod having a flattened distal end which is pivotally connected to the movable portion of the tip assembly.

13. A surgical instrument according to claim 12, wherein said movable portion of the tip assembly is provided with a slot which receives the distal end of the wire rod, and wherein the distal end of the wire rod is pivotally attached to opposing sidewalls of the slot.

14. A surgical instrument according to claim 13, wherein the pivotable connection between the wire rod and the movable portion of the tip assembly is disposed between the parallel planes which extend through the pivot pin.

15. A surgical instrument according to claim 11, wherein said stationary portion comprises a first cutting edge extending substantially parallel to and laterally adjacent the longitudinal axis of the support shaft, and a second cutting edge extending substantially transversely to the longitudinal axis of the support shaft, and wherein said movable portion comprises first and second curing edges which cooperate, respectively, with the first and second curing edges of the stationary portion.

16. A surgical instrument according to claim 15, wherein said stationary portion comprises a third cutting edge extending substantially parallel to said first cutting edge and intersecting an end of the second cutting edge to define an area bounded on three sides by said first, second and third curing edges, and said movable portion comprising a third cutting edge which cooperates with the third cutting edge of the stationary portion.

17. A surgical instrument according to claim 11, wherein said opposing sidewalls extend laterally adjacent and substantially parallel to the longitudinal axis of the support shaft, and wherein said sidewalls have openings formed therein for receiving respective ends of the pivot pin which extends through, and forms a pivot axis of, said movable portion of the tip assembly.

18. A surgical instrument according to claim 17, wherein said stationary portion further comprises a third sidewall extending substantially orthogonally between distal ends of said opposing sidewalls.

* * * * *